United States Patent
Wei et al.

(10) Patent No.: US 9,915,557 B2
(45) Date of Patent: Mar. 13, 2018

(54) ULTRASONIC WAVE SENSING MODULE

(71) Applicant: Magna Electronics Solutions GmbH, Wetzlar (DE)

(72) Inventors: Jingyuan Wei, Taipei (TW); Jiayu Lin, Taipei (TW)

(73) Assignee: MAGNA ELECTRONICS SOLUTIONS GMBH, Wetzlar (DE)

( * ) Notice: Subject to any disclaimer, the term of this patent is extended or adjusted under 35 U.S.C. 154(b) by 234 days.

(21) Appl. No.: 14/707,552

(22) Filed: May 8, 2015

(65) Prior Publication Data

US 2015/0323504 A1   Nov. 12, 2015

(30) Foreign Application Priority Data

May 8, 2014  (CN) .......................... 2014 1 0191943

(51) Int. Cl.
| | |
|---|---|
| G01F 1/66 | (2006.01) |
| G01N 29/22 | (2006.01) |
| G01S 15/93 | (2006.01) |
| G01S 7/521 | (2006.01) |
| G01S 15/96 | (2006.01) |

(52) U.S. Cl.
CPC ............. G01F 1/66 (2013.01); G01N 29/223 (2013.01); G01S 7/521 (2013.01); G01S 15/931 (2013.01); *G01N 2291/101* (2013.01); *G01S 15/96* (2013.01)

(58) Field of Classification Search
CPC .. G01N 29/22; G01N 29/222; G01N 29/2437; G01N 29/2487; G01D 11/245; G01S 7/521; G01S 15/96; G01S 15/931

USPC ........ 73/632, 641, 866.5; 310/338; 367/140; 361/752
See application file for complete search history.

(56) References Cited

U.S. PATENT DOCUMENTS

| | | | | |
|---|---|---|---|---|
| 5,767,773 | A * | 6/1998 | Fujiuchi | G08B 13/1454 340/571 |
| 6,862,932 | B2 * | 3/2005 | Zimmermann | G01F 23/246 73/290 R |
| 2007/0230273 | A1 * | 10/2007 | Nakajima | G01S 7/521 367/140 |
| 2007/0237031 | A1 * | 10/2007 | Kawashima | G10K 9/22 367/140 |

(Continued)

*Primary Examiner* — Manish S Shah
*Assistant Examiner* — Suman K Nath
(74) *Attorney, Agent, or Firm* — Gardner, Linn, Burkhart & Flory, LLP

(57) ABSTRACT

An ultrasonic wave sensing module includes a housing, an ultrasonic wave sensor, an adapter, and a circuit board. The housing has a first containing space and a second containing space being separated from each other by a blocking wall. The ultrasonic wave sensor is disposed within the first containing space and has a first connecting pin. The adapter includes a first connecting portion and a second connecting pin, and is integrally formed with the blocking wall by means of insert molding. The circuit board is provided within the second containing space, and has a second connecting portion. The first connecting pin of the ultrasonic wave sensor is coupled to the first connecting portion of the adapter, and the second connecting pin of the adapter is coupled to the second connecting portion of the circuit board, so that the ultrasonic wave sensor and the circuit board are electrically connected.

20 Claims, 3 Drawing Sheets

(56) References Cited

U.S. PATENT DOCUMENTS

| | | | |
|---|---|---|---|
| 2010/0139389 A1* | 6/2010 | Morita | G01F 5/00 73/204.11 |
| 2012/0243189 A1* | 9/2012 | Urase | G10K 11/004 361/752 |
| 2015/0331100 A1 | 11/2015 | Hsu et al. | |

* cited by examiner

ULTRASONIC WAVE SENSING MODULE

CROSS-REFERENCE TO RELATED APPLICATION

The present application claims the benefit of Chinese Patent Application No. 201410191943.7, filed on May 8, 2014 in the State Intellectual Property Office of China, the disclosure of which is incorporated herein by reference in its entirety.

BACKGROUND OF THE INVENTION

Field of the Invention

The present disclosure relates to an ultrasonic wave sensing module, and more particularly, to an ultrasonic wave sensing module for detecting objects.

Description of Related Art

Any sonic waves or vibrations having a frequency larger than a highest threshold of about 20 KHz that can be heard by ears of human being, are commonly referred to as ultrasonic waves. The ultrasonic wave has been widely applied in many fields, such as radar positioning, medical diagnosis, or distance measurement. Taking the distance measurement as an example, an emitter may be used to emit ultrasonic waves toward a certain direction. The timekeeping is started at the time when ultrasonic waves are emitted. And then, the ultrasonic waves will propagate in the air, and will be reflected back upon colliding with barriers. The timekeeping is stopped once a receiver receives the reflected waves. Thus, a distance of the emitting location from the barrier can be calculated by a traveling speed of the ultrasonic wave and a time length of the timekeeping.

SUMMARY OF THE INVENTION

The present disclosure relates to an ultrasonic wave sensing module, wherein an adapter is used to connect an ultrasonic wave sensor with a circuit board. This simplifies the assembling process and improves the waterproof effect.

In accordance with an embodiment of the present invention, an ultrasonic wave sensing module includes a housing, an ultrasonic wave sensor, an adapter, and a circuit board. The housing has a first containing space and a second containing space being separated from each other by a blocking wall. The ultrasonic wave sensor is disposed within the first containing space and has a first connecting pin. The adapter includes a first connecting portion and a second connecting pin, and is integrally formed with the blocking wall by means of insert molding. The circuit board is provided within the second containing space, and has a second connecting portion. The first connecting pin of the ultrasonic wave sensor is coupled to the first connecting portion of the adapter, and the second connecting pin of the adapter is coupled to the second connecting portion of the circuit board, so that the ultrasonic wave sensor and the circuit board are electrically connected.

BRIEF DESCRIPTION OF THE DRAWINGS

In order to better understand the above aspects and other aspects of the present invention, the detailed description is set out therein in conjunction with the specific embodiments with reference to the attached drawings, wherein.

DETAILED DESCRIPTION OF PREFERRED EMBODIMENT

Embodiments of the present invention will be described in detail with reference to the attached drawings. The same reference numbers in the figures are used to indicate the same or similar parts. It should be noted that the figures are drawn in a simplified way, for sake of clearly illustrating contents of the present embodiments, and dimension scale in the attached figures is not drawn in the same proportion with the practical products, thus it is not intended to limit the scope of the present invention.

Figure 1:
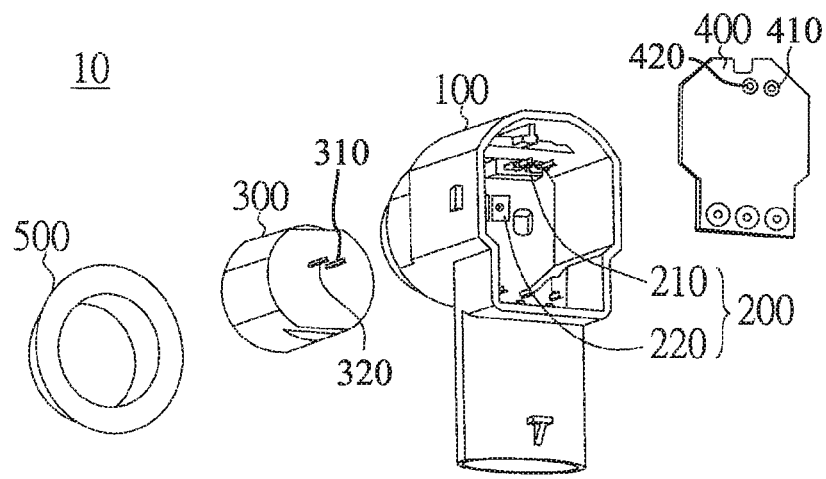
FIG. 1 shows a prospective exploded view of an ultrasonic wave sensing module in accordance with an embodiment of the present invention.

With reference to FIG. 1, it shows a prospective exploded view of an ultrasonic wave sensing module in accordance with an embodiment of the present invention. The ultrasonic wave sensing module 10 is, for example, a distance sensor, applicable to various prevention devices (for example, reversing radar of a car) or detection devices (for example, non-destructive inspection, sonar, fish detection), but the present invention is not limited to those. The ultrasonic wave sensing module includes a housing 100, an adapter 200, an ultrasonic wave sensor 300, and a circuit board 400. The housing 100 functions for protection, and is used to accommodate the components, such as the adapter 200, the ultrasonic wave sensor 300, and the circuit board 400, in order to prevent foreign matters such as dusts or moisture entering therein. The adapter 200 is used to connect the ultrasonic wave sensor 300 with the circuit board 400. The ultrasonic wave sensor 300 can emit and receive the ultrasonic waves. The circuit board 400 includes various circuit elements (not shown), like a driver integrated circuit (IC) thereon, which can be used to manipulate the ultrasonic wave sensor 300 and process the received signals. In addition, the ultrasonic wave sensing module 10 may also include a rubber pad or ring 500 surrounding the ultrasonic wave sensor 300, so that the ultrasonic wave sensor 300 can be more firmly fixed into the housing 100, the influence of the vibrations to the ultrasonic wave sensor 300 can be reduced, and the risk of moisture or dusts entering the housing 100 can be decreased.

Figure 2:
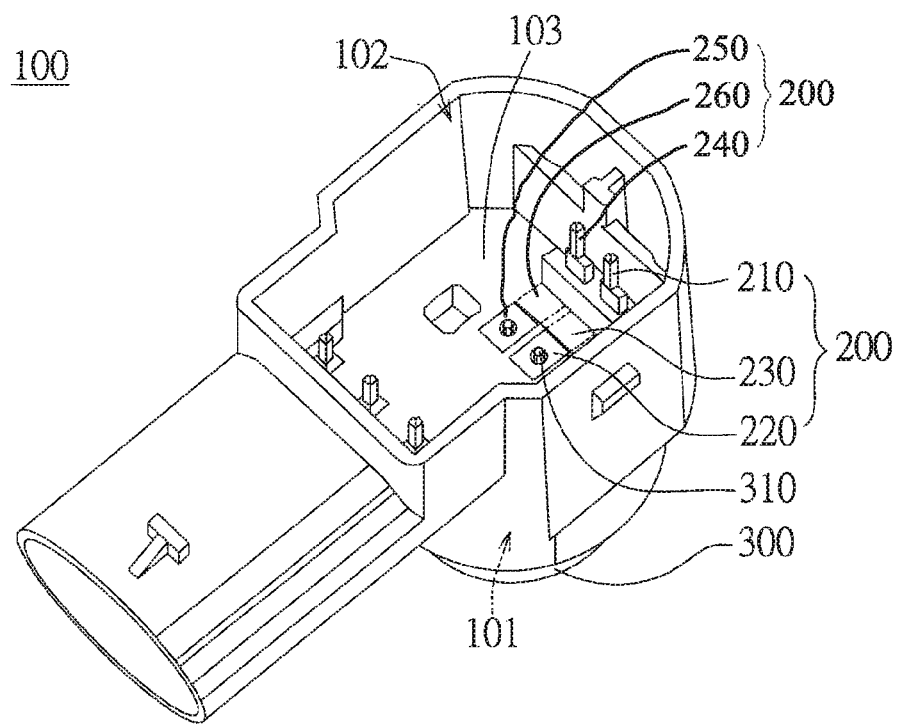
FIG. 2 shows a schematic view of a housing and an ultrasonic wave sensor assembled together, within the ultrasonic wave sensing module as shown in FIG. 1.

With reference to FIG. 2, it shows a schematic view of the assembled housing 100 and ultrasonic wave sensor 300, within the ultrasonic wave sensing module 10 as shown in FIG. 1. The housing 100 has a first containing space 101 and a second containing space 102, which are separated from each other by a blocking wall 103. The first containing space 101 can be used to accommodate the ultrasonic wave sensor 300 and the rubber pad 500 (please see FIG. 1), and the second containing space 102 can be used to accommodate the circuit board 400 (please see FIG. 1). The housing 100 in the present embodiment has a shape like a T-shaped connection pipe. In addition to two arms of the T-shaped connection pipe having the respective containing spaces, the bottom thereof is also provided with an additional containing space, which is configured to connect other elements such as the power supply. However, the present invention does not limit the shape of the housing, and any shapes having two containing spaces for accommodating the ultrasonic wave sensor and the circuit board respectively are feasible for the housing of the present disclosure. The blocking wall 103 separates the first containing space 101 from the second containing space 102, and the adapter 200 located in the blocking wall 103 electrically connects the ultrasonic wave sensor 300 in the first containing space 101 with the circuit board 400 in the second containing space 102.

With reference to FIGS. 1 and 2 together, the adapter 200 is located inside the blocking wall 103, and includes a second connecting pin 210 and a first connecting portion 220. The method of disposing the adapter 200 into the blocking wall 103 is for example an insert molding. The insert molding is a molding technique for plastics. An insert part (the adapter 200 herein) is placed into the mold, and then the plastic is charged into the mold, so that the insert and the coated part (plastic) are integrally formed. Thus, the present disclosure omits secondary manufacturing process such as adhering and assembling processes, compared with the conventional assembling way in which an additional fixing piece is needed to fix the connecting pin. The insert molding method employed by the present embodiment not only shortens the assembling time, but also saves costs of the parts. Furthermore, the manufacturing process of insert molding can reduce opening area of the holes on the blocking wall for the assembling, so that the separation between the first containing space 101 and the second containing space 102 are enhanced, and waterproof and dustproof effects of the housing 110 to the circuit board 400 can be improved.

As shown in FIGS. 1 and 2, the second connecting pin or portion 210 of the adapter 200 is used to be connected with the first engaging or connecting portion 410 of the circuit board 400, whereas the first connecting portion 220 of the adapter 200 is used to be connected with a first connecting pin 310 of the ultrasonic wave sensor 300, so that the ultrasonic wave sensor 300 is electrically connected with the circuit board 400. Similarly, as shown in FIGS. 1 and 2, the fourth connecting pin or portion 240 of the adapter 200 is used to be connected with the second engaging or connecting portion 420 of the circuit board 400, whereas the third connecting portion 250 of the adapter 200 is used to be connected with a second connecting pin 320 of the ultrasonic wave sensor 300, so that the ultrasonic wave sensor 300 is electrically connected with the circuit board 400. In the present embodiment, the first and second connecting pins 310, 320 of the ultrasonic wave sensor 300 and the second and fourth connecting pins or portions 210, 240 are needle-shaped connecting pins, and the first and second connecting portions 220, 250 of the adapter 200 and the first and second engaging or connecting portions 410, 420 are jacks. The needle-shaped connecting pins can be inserted into the jacks, and be fixed by the means of welding or the like. It should be especially noted that the present invention does not limit the number and shapes of the connecting portions and the connecting pins. For example, in other embodiments, the connecting portions and the connecting pins can be connecting pads, and are fixed together by contacting, magnetic force or adhesives.

As shown in FIG. 2, the second connecting pin or portion 210 and the first connecting portion 220 of the adapter 200 can be provided at different positions on the blocking wall 103 respectively, and they are electrically connected via a first extension portion 230. Similarly, as shown in FIG. 2, the fourth connecting pin or portion 240 and the third connecting portion 250 of the adapter 200 can be provided at different positions on the blocking wall 103 respectively, and they are electrically connected via a second extension portion 260. In this way, the position of the first and second engaging or connecting portions 410, 420 on the circuit board 400 do not necessarily correspond, respectively, to that of the first and second connecting pins 310, 320 on the ultrasonic wave sensor 300 (as shown in FIG. 1), so that the circuit design of the circuit board 400 is more flexible.

Figure 3:
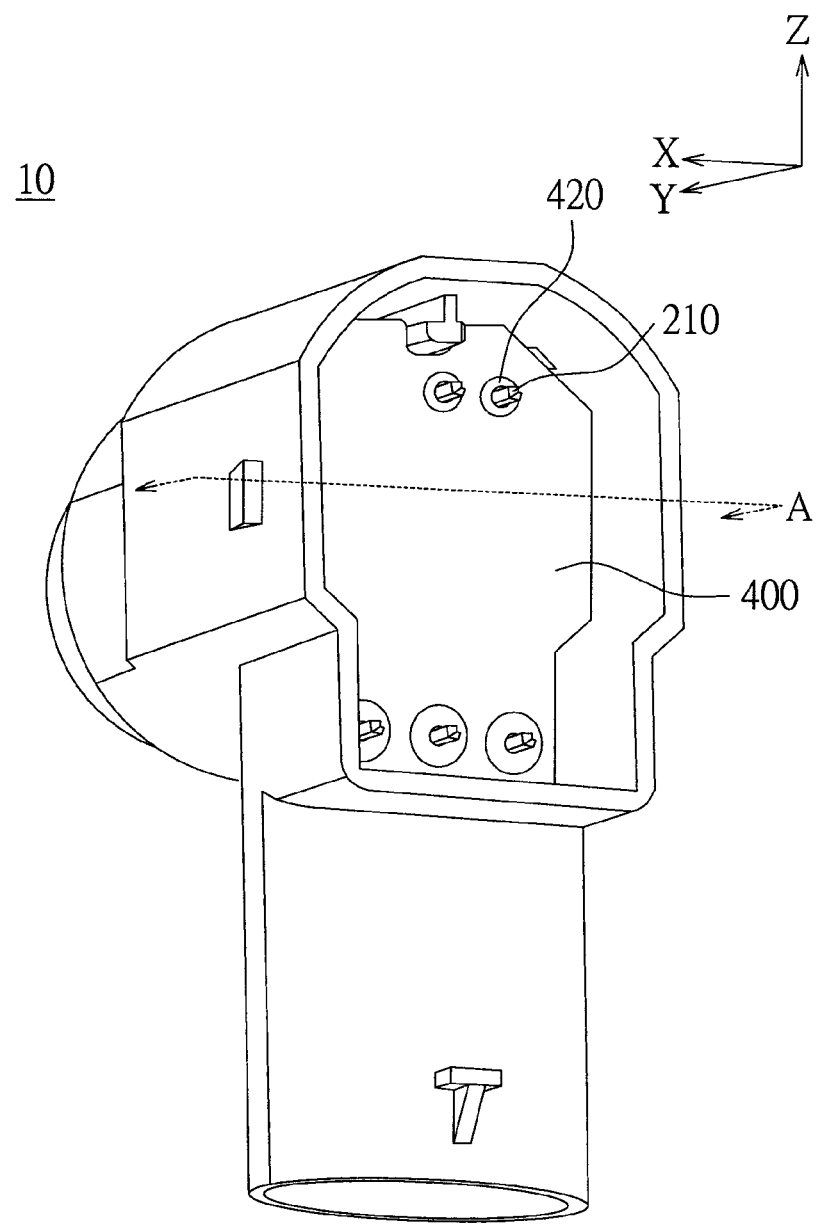
FIG. 3 shows a schematic view of the housing, the ultrasonic wave sensor, and a circuit board assembled together, within the ultrasonic wave sensing module as shown in FIG. 1.

With reference to FIGS. 1 and 3, specifically, FIG. 3 shows a schematic view of the housing 100, the ultrasonic wave sensor 300, and the circuit board 400 that have been assembled, within the ultrasonic wave sensing module 10 as shown in FIG. 1. As described above, the first and second engaging or connecting portion 410, 420 of the circuit board 400 can be a jack, and the second and fourth connecting pins or portions 210, 240 of the adapter 200 are inserted and welded into the jack. The circuit board 400 can includes other circuit elements like other connecting portions, connecting pins, jacks, or processors, so as to drive the ultrasonic wave sensing module 10.

Figure 4A:
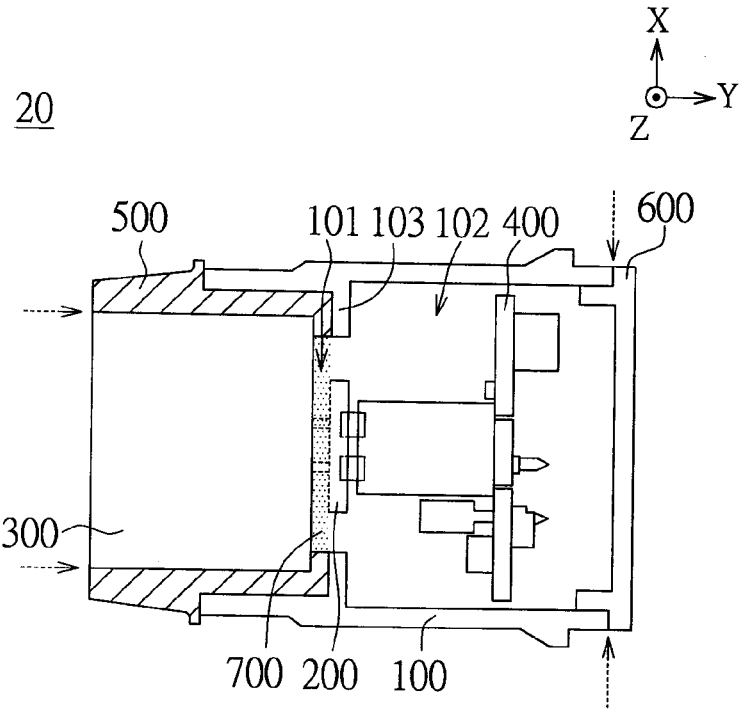
FIG. 4A shows a sectional view of the assembled ultrasonic wave sensing module, taken at line A-A of the embodiment shown in FIG. 3.

With reference to FIG. 4A, it shows a sectional view of the assembled ultrasonic wave sensing module in accordance with another embodiment of the present invention, the sectional direction of which substantially corresponds to a sectional line A-A of FIG. 3. The ultrasonic wave sensing module 20 of the present embodiment makes an improvement on the waterproof function. Since the remaining structures thereof are similar to those of the above ultrasonic wave sensing module 10, they are omitted herein.

As shown in FIG. 4A, the first containing space 101 of the ultrasonic wave sensing module 20 (in order to accommodate the ultrasonic wave sensor 300) is filled with waterproof glue 700. The waterproof glue 700 is for example polyurethane (PU) glue or other insulating glues for blocking the moisture, such as hot-melt adhesive made by low pressure molding. The waterproof glue 700 covers the connecting pin of the ultrasonic wave sensor 300, and blocks the opening holes in the blocking wall 103. In this way, the moisture entering from the ultrasonic wave sensor 300 (the dotted arrow indicates a path along which the moisture might enter) will be blocked by the waterproof glue 700, instead of contacting with the connecting pin or the circuit board, and thus short circuit caused by it may be avoided. In the present embodiment, the first containing space 101 is filled with the waterproof glue 700, but in other embodiments, the blocking wall 103 or the second containing space 102 may also be filled with it, so as to further block the moisture.

As shown in FIG. 4A, the second containing space 102 of the ultrasonic wave sensing module 20 is sealed by a sealing cover 600, which can prevent the moisture entering the second containing space 102 and resulting in the short circuit of the circuit board 400. The contacting portions of the sealing cover 600 with the housing 100 can be joined by means of ultrasonic wave welding or the like, so that the sealing cover 600 and the housing 100 become integral, and this prevents the moisture or dusts entering the second containing space 102 from the engagement thereof (along the dotted arrow). The designs of the sealing cover 600 and the waterproof glue 700 can reduce the contact area of the ultrasonic wave sensing module 20 with the external environment, and thus decrease the entering risk of the moisture or the dusts.

Figure 4B:
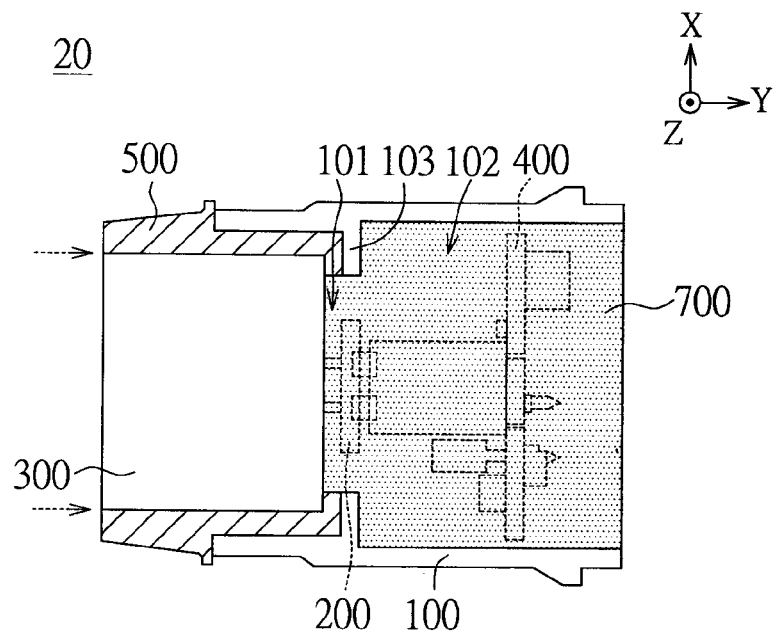
FIG. 4B shows a sectional view of the assembled ultrasonic wave sensing module, in accordance with another embodiment of the present invention.

With reference to FIG. 4B, it shows a sectional view of the assembled ultrasonic wave sensing module in accordance with another embodiment of the present invention. The ultrasonic wave sensing module 30 is also designed to improve the waterproof thereof.

As shown in FIG. 4B, the first containing space 101, the second containing space 102, and the opening holes of the blocking wall 103 are filled with the waterproof glue 700. This figure shows the entire interior of the housing 100 filled up with the waterproof glue 700, but in practice, the blocking effect can be obtained as long as the waterproof glue 700 covers the circuit elements. In this circumstance, even if the moisture enters the housing 100, the short circuit in the ultrasonic wave sensor 300, the adapter 200 or the circuit board 400 would not occur.

With the ultrasonic wave sensing modules in accordance with the above embodiments, the adapter which is formed into the interior blocking wall of the housing by the insert molding, connects the ultrasonic wave sensor with the circuit board. This makes the circuit design of the circuit board to be more flexible, improves the shielding effect of the blocking wall, and simplifies the assembling process as well as reduces the costs of the parts. In addition, the containing spaces of the housing are sealed by the additionally provided sealing cover or waterproof glue, so that the waterproof and dustproof effects of the ultrasonic wave sensing module can be enhanced significantly. Therefore, it can normally function in various special working conditions.

Concerning the above, the embodiments of the present invention are disclosed as described above, but they are not intended to limit the present invention. The skilled person in the art having ordinary knowledge would make various variants and modifications, without departing from the sprits and scope of the present invention. Therefore, the protection scope of the present invention should be defined and delimited by the attached claims.

What is claimed is:

1. An ultrasonic wave sensing module, comprising:
a housing having a first containing space and a second containing space separated from each other by a blocking wall, wherein the blocking wall has a first side surface forming an interior surface of the first containing space and a second side surface opposing the first side surface and forming an interior surface of the second containing space;
an ultrasonic wave sensor disposed in the first containing space and having a first connecting pin that extends into the blocking wall and a second connecting pin that extends into the blocking wall;
an adapter comprising a first connecting portion, a second connecting portion, a third connecting portion, and a fourth connecting portion, wherein the first connecting portion is electrically connected with the second connecting portion via a first extension portion of the adapter, and wherein the third connecting portion is electrically connected with the fourth connecting portion via a second extension portion of the adapter;
a circuit board disposed in the second containing space and having a first engaging portion and a second engaging portion;
wherein at least the first extension portion of the adapter and the second extension portion of the adapter are integrally formed with the blocking wall via insert molding;
wherein the first extension portion of the adapter and the second extension portion of the adapter are electrically isolated from one another by material of the blocking wall;
wherein the first connecting pin of the ultrasonic wave sensor is coupled to the first connecting portion of the adapter at least partially between the first and second side surfaces of the blocking wall, and wherein the second connecting pin of the ultrasonic wave sensor is coupled to the third connecting portion of the adapter at least partially between the first and second side surfaces of the blocking wall; and
wherein the second connecting portion of the adapter is coupled to the first engaging portion of the circuit board, and wherein the fourth connecting portion of the adapter is coupled to the second engaging portion of the circuit board, so that the first and second connecting pins of the ultrasonic wave sensor are electrically isolated from one another by material of the blocking wall and are electrically connected respectively with first and second engaging portions of the circuit board via the adapter.

2. The ultrasonic wave sensing module of claim 1, wherein the first extension portion locates the first connecting portion and the second connecting portion of the adapter at different positions on the blocking wall.

3. The ultrasonic wave sensing module of claim 1, further comprising:
a rubber ring secured between the ultrasonic wave sensor and the first containing space.

4. The ultrasonic wave sensing module of claim 1, further comprising:
waterproof glue substantially filling at least one of the first containing space or the second containing space for protecting the respective ultrasonic wave sensor or circuit board from exposure to moisture.

5. The ultrasonic wave sensing module of claim 4, wherein the waterproof glue comprises at least one of polyurethane glue or hot-melt adhesive.

6. The ultrasonic wave sensing module of claim 1, wherein the second and fourth connecting portions of the adapter each comprise a needle-shape that extends through and engages the respective first and second engaging portions of the circuit board.

7. The ultrasonic wave sensing module of claim 4, wherein, when the first containing space is filled with the waterproof glue, the ultrasonic wave sensing module further comprises a sealing cover coupled with the housing and substantially sealing the second containing space of the housing.

8. The ultrasonic wave sensing module of claim 7, wherein the sealing cover is coupled via ultrasonic welding to the housing.

9. The ultrasonic wave sensing module of claim 1, wherein the first and second connecting pins of the ultrasonic wave sensor are coupled to the first and third connecting portions of the adapter by welding, and wherein the second and fourth connecting portions of the adapter are coupled to the respective first and second engaging portions of the circuit board by welding.

10. The ultrasonic wave sensing module of claim 9, wherein the first and third connecting portions and the first and second engaging portions include jacks, and wherein the first and second connecting pins and the second and fourth connecting portions are inserted and welded into the jacks.

11. The ultrasonic wave sensing module of claim 1, wherein the blocking wall has at least one opening hole at each of the first and third connecting portions of the adapter, and wherein the first and second connecting pins of the ultrasonic wave sensor extend through the corresponding opening hole to couple with the respective first and third connecting portions of the adapter.

12. The ultrasonic wave sensing module of claim 1, wherein said first and second connecting portions and said first extension portion of the adapter together comprise a single piece of conductive material that is integrally formed with the blocking wall via insert molding.

13. An ultrasonic wave sensing module, comprising:
a housing having a blocking wall that separates a first containing space from a second containing space, wherein the blocking wall has a first side surface disposed at the first containing space and a second side surface opposing the first side surface and disposed at the second containing space;
an adapter disposed at least partially between the first and second side surfaces of the blocking wall, wherein the adapter comprises a first connecting portion, a second connecting portion, a third connecting portion, and a fourth connecting portion;
wherein the first connecting portion of the adapter is electrically connected with the second connecting portion via a first extension portion of the adapter, and wherein the third connecting portion of the adapter is electrically connected with the fourth connecting portion via a second extension portion of the adapter;
wherein the first connecting portion and the third connecting portion are exposed to the first containing space, and wherein the second connecting portion and the fourth connecting portion are exposed to the second containing space;
wherein at least the first extension portion of the adapter and the second extension portion of the adapter are integrally formed with the blocking wall via insert molding and are disposed within the blocking wall;
wherein the first extension portion of the adapter and the second extension portion of the adapter are electrically isolated from one another by material of the blocking wall;
an ultrasonic wave sensor comprising a first connecting pin coupled with the first connecting portion and a second connecting pin coupled with the third connecting portion, wherein the ultrasonic wave sensor electrically interfaces with the adapter at least partially between the first and second side surfaces of the blocking wall; and
a circuit board coupled with the second connecting portion and the fourth connecting portion, wherein the ultrasonic wave sensor is electrically connected to the circuit board via the adapter.

14. The ultrasonic wave sensing module of claim 13, wherein the first extension portion offsets the first connecting portion and the second connecting portion on the blocking wall.

15. The ultrasonic wave sensing module of claim 13, wherein the adapter is integrally formed with the blocking wall via insert molding, and wherein the first connecting portion includes one of a pin or a jack.

16. The ultrasonic wave sensing module of claim 13, further comprising waterproof glue substantially filling at least one of the first containing space or the second containing space for protecting the respective ultrasonic wave sensor and circuit board from exposure to moisture.

17. An ultrasonic wave sensing module, comprising:
a housing having a blocking wall that separates a first containing space from a second containing space, wherein the blocking wall has a first side surface disposed at the first containing space and a second side surface opposing the first side surface and disposed at the second containing space, and wherein the first side surface is substantially parallel with the second side surface;
an ultrasonic wave sensor coupled with the first containing space of the housing to sealingly prevent moisture from entering the first containing space;
a circuit board disposed in the second containing space of the housing, wherein the ultrasonic wave sensor is electrically connected to the circuit board through the blocking wall via an adapter that is at least partially disposed between the first and second side surfaces of the blocking wall;
wherein the adapter comprises a first connecting portion, a second connecting portion, a third connecting portion, and a fourth connecting portion;
wherein the first connecting portion of the adapter is electrically connected with the second connecting portion via a first extension portion of the adapter, and wherein the third connecting portion of the adapter is electrically connected with the fourth connecting portion via a second extension portion of the adapter;
wherein the first connecting portion and the third connecting portion are exposed to the first containing space, and wherein the second connecting portion and the fourth connecting portion are exposed to the second containing space;
wherein at least the first extension portion of the adapter and the second extension portion of the adapter are integrally formed with the blocking wall via insert molding and are disposed within the blocking wall; and
wherein the first extension portion of the adapter and the second extension portion of the adapter are electrically isolated from one another by material of the blocking wall.

18. The ultrasonic wave sensing module of claim 17, wherein the second containing space comprises a sealing to prevent the circuit board from being exposed to moisture.

19. The ultrasonic wave sensing module of claim 18, wherein the sealing includes at least one of a cover coupled with the housing or a waterproof glue disposed in the second containing space.

20. The ultrasonic wave sensing module of claim 17, wherein at least one of the ultrasonic wave sensor or the circuit board is coupled to the adapter by a pin engaging a jack.

* * * * *